(12) United States Patent
Balzar et al.

(10) Patent No.: US 6,293,932 B1
(45) Date of Patent: *Sep. 25, 2001

(54) INDIVIDUALLY WRAPPED ABSORBENT ARTICLE WHICH USES A MINIMUM AMOUNT OF WRAPPER MATERIAL

(75) Inventors: Tammy Jo Balzar, Menasha; Janet Jessie Larsen, Neenah; James Dell Milner, Appleton; Valerie Victoria Finch, Neenah; Pamela Jean DeShaney, Readfield, all of WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 09/057,852

(22) Filed: Apr. 9, 1998

(51) Int. Cl.$^7$ ..................................................... A61F 13/15
(52) U.S. Cl. ............................... 604/385.02; 604/385.01; 604/385.03; 604/385.05; 604/385.13; 604/389; 604/387; 206/440
(58) Field of Search ................... 604/385.01, 385.02, 604/385.03, 385.05, 385.11, 385.13, 389, 391; 206/440

(56) References Cited

U.S. PATENT DOCUMENTS

| | | |
|---|---|---|
| H1363 | 10/1994 | Leeker . |
| H1454 | 6/1995 | Cucuzza et al. ................. 604/385.1 |
| 3,561,593 | 2/1971 | Ruda ....................................... 206/57 |

(List continued on next page.)

FOREIGN PATENT DOCUMENTS

| | | |
|---|---|---|
| 4127411 C1 | 1/1992 | (DE) . |
| 0 750 896 A3 | 1/1997 | (EP) ............................. A61F/13/15 |
| 0 798 229 A1 | 1/1997 | (EP) . |

(List continued on next page.)

Primary Examiner—John G. Weiss
Assistant Examiner—Michele Kidwell
(74) Attorney, Agent, or Firm—Thomas M. Parker (57) ABSTRACT

An individually wrapped absorbent article, such as a catamenial device, is disclosed. The absorbent article has first and second ends, first and second longitudinal sides and first and second major surfaces. The second major surface has a garment attachment adhesive secured thereto. The absorbent article is enclosed by a wrapper having first and second ends, first and second longitudinal sides and first and second major surfaces. The first major surface of the wrapper is releasably affixed to the garment attachment adhesive such that the first end of the absorbent article at a minimum is flush with the first end of the wrapper. When so attached, the second end of the wrapper will extend beyond the second end of the absorbent article and the first and second sides of the wrapper will extend laterally outward from the first and second sides of the absorbent article, respectively. An attachment device is secured to the second major surface of the wrapper approximate the first end. The wrapper and the absorbent article are folded together about two fold axes such that the first major surface of the wrapper contacts the attachment device and is releaseably secured thereto to form a package. The package has first and second side edges aligned approximately parallel to the first and second longitudinal sides of the absorbent article, respectively. A first seal and a second seal secure the first and second side edges together. The package further contains at least one line of perforations formed in the wrapper adjacent to and inward from one of the first and second seals. The line of perforations provide an easy open feature for the package.

31 Claims, 8 Drawing Sheets

U.S. PATENT DOCUMENTS

| | | | |
|---|---|---|---|
| 3,698,549 | 10/1972 | Glassman | 206/63.2 R |
| 3,973,567 | 8/1976 | Srinivasan et al. | 128/290 R |
| 4,170,305 | 10/1979 | Hull, Jr. et al. | 206/606 |
| 4,556,146 | 12/1985 | Swanson et al. | 206/440 |
| 5,037,417 | 8/1991 | Ternstrom et al. . | |
| 5,088,993 | 2/1992 | Gaur . | |
| 5,181,610 | 1/1993 | Quick et al. | 206/447 |
| 5,413,568 | 5/1995 | Roach et al. . | |
| 5,445,454 | 8/1995 | Barkhorn | 383/207 |
| 5,478,336 | 12/1995 | Pigneul . | |
| 5,484,636 | 1/1996 | Berg, Jr. et al. . | |
| 5,569,228 | 10/1996 | Byrd et al. . | |
| 5,569,230 | 10/1996 | Fisher et al. . | |
| 5,954,201 * | 9/1999 | Finch et al. | 206/440 |
| 5,993,430 | 11/1999 | Gossens et al. . | |
| 6,036,679 | 3/2000 | Balzar et al. . | |

FOREIGN PATENT DOCUMENTS

| | | | |
|---|---|---|---|
| 2 153 779 | 8/1985 | (GB) . | |
| 2273279 | 6/1994 | (GB) | B65D/85/16 |
| 2277914 | 11/1994 | (GB) . | |
| 2300402 | 6/1996 | (GB) . | |
| WO 91/18574 A1 | 12/1991 | (WO) . | |
| WO 93/09743 A1 | 5/1993 | (WO) . | |
| WO 94/04111 | 3/1994 | (WO) . | |
| WO 94/14396 A1 | 6/1994 | (WO) . | |
| WO 97/12572 A1 | 4/1997 | (WO) | A61F/13/15 |

* cited by examiner

INDIVIDUALLY WRAPPED ABSORBENT ARTICLE WHICH USES A MINIMUM AMOUNT OF WRAPPER MATERIAL

FIELD OF THE INVENTION

This invention relates to an individually wrapped absorbent article, such as a catamenial pad, which uses a minimum amount of wrapper material. More specifically, this invention relates to an absorbent article which has a first end which at a minimum is aligned flush with the first end of the wrapper before the absorbent article and wrapper are folded so as to reduce the amount of wrapper material which is needed.

BACKGROUND OF THE INVENTION

Absorbent articles such as sanitary napkins, panty liners, and other types of catamenial devices are used to absorb menses and other body fluids. Such absorbent articles are primarily disposable and are used during a women's menstrual cycle. In addition, disposable absorbent articles are used between menstrual periods for light incontinence purposes. Since many of these absorbent articles are carried in a woman's purse or pocket prior to use, it is advantageous to individually wrap each article so as to keep it clean. By individually packaging each absorbent article, the manufacturer can be assured that the article will not become contaminated by makeup, perfume, dirt, etc. Because of this, many absorbent articles commercially sold today are individually packaged.

Generally, the wrapper consists of a thin sheet of thermoplastic material, such as polyethylene, which is folded around the absorbent article and is then sealed by the use of heat and/or pressure, by ultrasonics or by an adhesive, to form a package. The package is designed to be opened by breaking or tearing the material at or adjacent the seal so as to remove the absorbent article. Normally, the thermoplastic material is designed to tear adjacent to the seal. However, when this occurs, the thermoplastic material acquires a ragged appearance and the tearing operation can be noisy. Most woman desire a package which can be quietly opened to avoid any embarrassing moments. In addition, it has been found that some seals are of a frangible nature such that they will come apart prior to use and therefore allow contamination to enter and contact the absorbent article. This is a detriment in that the consumer expects the absorbent article to be clean in appearance when she opens the package.

Another use for the wrapper is to enclose a soiled sanitary napkin after it has been used by the consumer so that it can be discretely disposed. For this reason, it is advantageous to design a package which can be opened such that a large piece of the wrapper material remains which can be used to wrap up a soiled sanitary napkin prior to its disposal.

In view of the above, it has been recognized that there is a need for an individually wrapped absorbent article which has an easy open feature and which can be quietly and discreetly opened. It is also advantageous to offer an individually wrapped absorbent article having one or more lines of perforations which enable the wrapper to be cleanly torn apart so that no ragged edges are present.

SUMMARY OF THE INVENTION

Briefly, this invention relates to an individually wrapped absorbent article, such as a catamenial device. The absorbent article has first and second ends, first and second longitudinal sides and first and second major surfaces. The second major surface has a garment attachment adhesive secured thereto. A wrapper having first and second ends, first and second longitudinal sides and first and second major surfaces is designed to enclose the absorbent article. To accomplish this, the first major surface of the wrapper is releaseably affixed to the garment attachment adhesive such that the first end of the absorbent article at a minimum is aligned flush the first end of the wrapper. When so attached, the second end of the wrapper will extend beyond the second end of the absorbent article and the first and second longitudinal sides of the wrapper will extend laterally outward from the first and second sides of the absorbent article, respectively. An attachment device is secured to the second major surface of the wrapper approximate the first end. The wrapper and the absorbent article are folded together about two fold axes such that the first major surface of the wrapper contacts the attachment device and is releaseably secured thereto to form a package. The package has first and second side edges aligned approximately parallel to the first and second sides of the absorbent article, respectively. A first seal and a second seal secure the first and second side edges together. The package further contains at least one line of perforations formed in the wrapper adjacent to and inward of the first and second seals, respectively. This line of perforations provide an easy open feature for the package.

The general object of this invention is to provide an individually wrapped absorbent article, such as a catamenial pad, which uses a minimum amount of wrapper material. A more specific object of this invention is to provide an absorbent article having a first end which is flush with the first end of the wrapper before the absorbent article and wrapper are folded so as to reduce the amount of wrapper material which is needed.

Another object of this invention is to provide an absorbent article having a first end which extends beyond the first end of the wrapper before the absorbent article and wrapper are folded so as to reduce the amount of wrapper material which is needed.

Another object of this invention is to provide an individually packaged absorbent article which is easy to assemble and is easy to open.

A further object of this invention is to provide an individually packaged absorbent article which allows the wrapper, after it has been removed from the absorbent article, to be used to discreetly dispose of a soiled sanitary napkin.

Still another object of this invention is to provide an individually packaged absorbent article with at least one line of perforations which can be easily broken in a discreet and quiet manner.

Still further, an object of this invention is to provide an individually packaged sanitary napkin or panty liner which includes a wrapper having first and second lines of perforations which extend along the entire length of the wrapper.

Other objects and advantages of the present invention will become more apparent to those skilled in the art in view of the following description and the accompanying drawings.

DETAILED DESCRIPTION OF THE PREFERRED EMBODIMENTS

Figure 1:
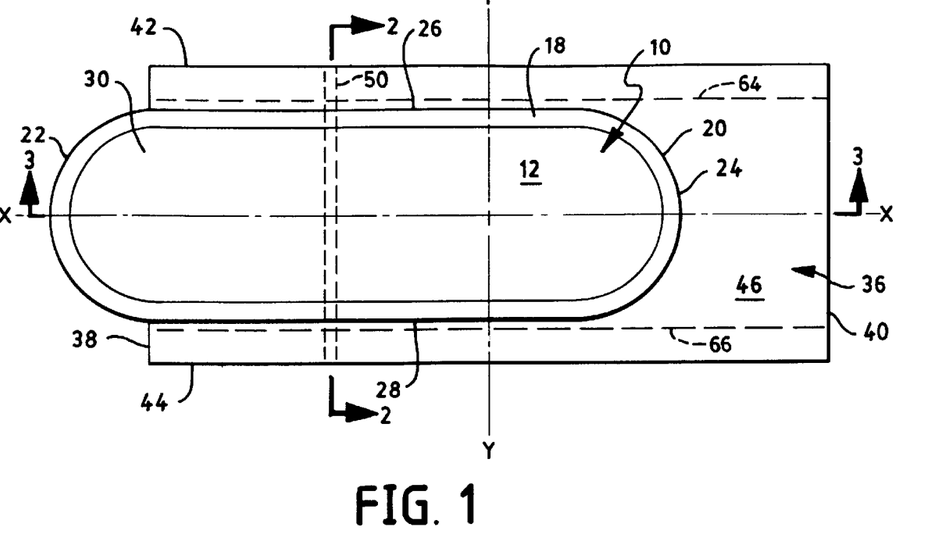
FIG. 1 is a top view of an absorbent article positioned above a rectangular shaped wrapper and offset thereon.
Figure 2:
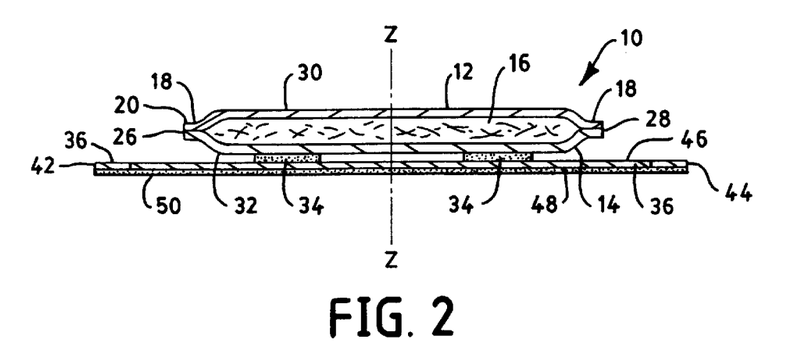
FIG. 2 is a cross-sectional view of the absorbent article and wrapper shown in FIG. 1 taken along line 2—2.
Figure 3:
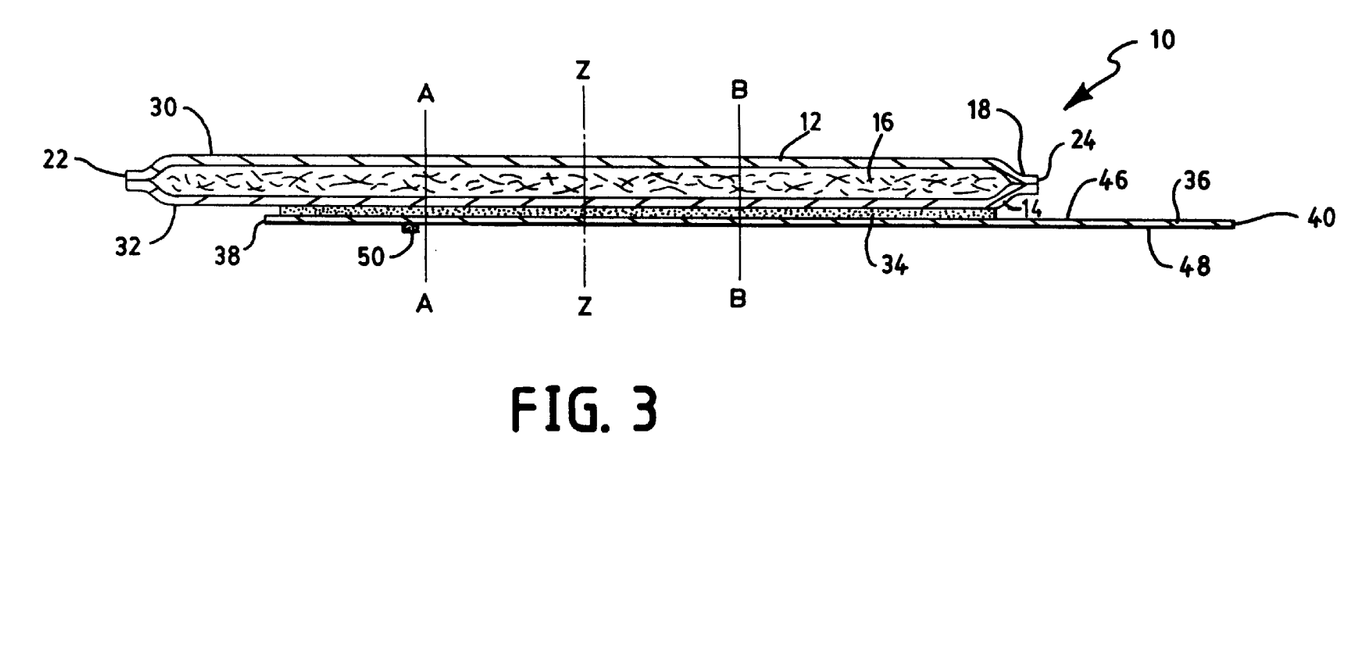
FIG. 3 is a cross-sectional view of the absorbent article and wrapper shown in FIG. 1 taken along line 3—3.

Referring to FIGS. 1, 2 and 3, an absorbent article 10 is shown. The absorbent article 10 can be a catamenial device such as a sanitary napkin, a panty liner, an incontinence pad, or any other type of absorbent article which can be used to absorb menstrual fluid, urine, body fluid, body exudate, etc. For purposes of describing this invention, the absorbent article 10 will be referred to as a sanitary napkin. The absorbent article 10 includes a liquid permeable cover 12, a liquid-impermeable baffle 14 and an absorbent 16. The cover 12 and the baffle 14 cooperate to enclose an absorbent 16. The cover 12 and the baffle 14 can extend beyond the outer periphery of the absorbent 16 to form a peripheral seal 18.

The peripheral seal 18 establishes the outer periphery 20 of the absorbent article 10.

The absorbent article 10 is an elongate member having a first end 22 and a second end 24 and a first longitudinal side 26 and a second longitudinal side 28. The first and second ends, 22 and 24 respectively, are spaced apart from one another as are the first and second longitudinal sides 26 and 28, respectively. The absorbent article 10 has a longitudinal central axis x—x, a transverse central axis y—y and a vertical axis z—z. The absorbent article 10 further contains a first major surface 30 and a second major surface 32. The first major surface 30 is designed to contact the body of the user while the second major surface 32 is spaced away from the body of the user. The second major surface 32 has a garment attachment adhesive 34 secured thereto. The garment attachment adhesive 34 is shown in FIG. 2 as being two separate strips of adhesive which are spaced apart from one another and which have a width of from about 0.25 inches to about 1 inch (about 6.4 mm to about 25 mm). The length of the adhesive strips 34 can extend over a major portion of the second major surface 32. The adhesive strips will preferably extend from between about 50 percent to about 95 percent of the length of the second major surface 32, as is shown in FIG. 3.

The absorbent article 10 is positioned on a wrapper 36 which can be a thin layer of material such as a thermoplastic film made from polypropylene, polyethylene or a laminate of two or more films. The wrapper 36 should be liquid-impermeable and have a thickness of less than about 5 mils, preferably less than about 3 mils, and more preferably, less than about 2 mils. The wrapper 36 is preferably formed from a polyethylene film having a thickness of less than about 2 mils. The wrapper 36 can be colored and/or contain a pattern. Preferred colors include white, peach and rose. Alternatively, the wrapper 36 can be made of different colors or be made of multiple colors if desired.

It should be noted that some absorbent articles which are commercially available use a releasable peel strip to cover the garment-facing adhesive. The present invention does not use a releasable peel strip and therefore provides several advantages. First, the absence of a peel strip provides a cost saving to the manufacturer. Second, the user does not have the added step of removing the peel strip prior to securing the absorbent article to her undergarment. A third advantage is that the absence of a peel strip reduces waste.

The wrapper 36 has a first end 38 and a second end 40, a first longitudinal side 42 and a second longitudinal side 44, and a first major surface 46 and a second major surface 48. The first and second ends, 38 and 40 respectively, are spaced apart from one another as are the first and second longitudinal sides 42 and 44, respectively. The first major surface 46 of the wrapper 36 is releasably affixed to the garment attachment adhesive 34 such that the first end 22 of the absorbent article 10 at a minimum is flush with the first end 38 of the wrapper 36, see FIG. 12. Preferably, the first end 22 of the absorbent article 10 extends beyond the first end 38 of the wrapper 36, as is shown in FIGS. 1 and 3. The second end 40 of the wrapper 36 extends beyond the second end 28 of the absorbent article 10 while the first and second longitudinal sides, 42 and 44 respectively, of the wrapper 36 extend outward beyond the outer periphery 20 of the absorbent article 10. The first end 22 of the absorbent article 10, when it is a sanitary napkin, can be flush with or extend beyond the first end 38 of the wrapper 36. When the first end 22 of the absorbent article 10 extends beyond the first end 38 of the wrapper 36, the distance can vary from between about 0.25 inches to about 2 inches (about 6.4 mm to about 50 mm). Preferably, the first end 22 of the absorbent article 10 will extend outward beyond the first end 38 of the wrapper 36 from about 0.5 inches to about 1 inch (about 13 mm to about 25 mm), and most preferably, from about 0.5 inches to about 0.75 inches (about 13 mm to about 19 mm). It should be noted that when the absorbent article 10 is other than a sanitary napkin or is an exceptionally long sanitary napkin, such as an overnight pad, the first end 22 of the absorbent article 10 can extend beyond the first end 38 of the wrapper 36 by more than about 2 inches (about 50 mm) if desired. It should also be noted that the above discussion describes the first end 22 of the absorbent article 10 being flush with or extending outward beyond the first end 38 of the wrapper 36. However, if one wanted to position the second end 24 of the absorbent article 10 flush with or have it extend beyond the second end 40 of the wrapper 36 that this is possible. If this is done, then the first end 38 of the wrapper 36 would extend outward beyond the first end 22 of the absorbent article 10.

By positioning the absorbent article 10 on the wrapper 36 such that one end of the absorbent article 10 is aligned flush with or extends outward beyond the respective end of the wrapper 36, it is possible to wrap the absorbent article 10 using less wrapper material than if the absorbent article 10 was centered on the wrapper 36. This is very important when one considers that absorbent articles, like sanitary napkins and panty liners, are manufactured at very high rates. For example, it is common to manufacture several hundreds sanitary napkins per minute on today's high speed equipment. With so many products, a small material saving on each article can result in significant cost savings over a years time.

The reduced need for wrapper material also means that a supply roll of wrapper material on a machine will last longer before it has to be replaced and this too equates into a cost saving from a production standpoint. Less labor will be needed because fewer changes of the supply roll of wrapper material will be needed and the frequency of such changes will be more spread out.

The individually wrapped absorbent article 10 further includes an attachment device 50 which is secured to the second major surface 48 of the wrapper 36. The attachment device 50 is located closer to the first end 38 of the wrapper 36 than to the second end 40. The attachment device 50 can be a spot of adhesive or a line of adhesive which extends transversely across the width of the wrapper 36. Optionally, the attachment device 50 can be one or more individual dots of adhesive which are separated from one another. The attachment device 50 can also include mechanical fasteners, Velcro fasteners, hook-and-loop fasteners, as well as other types of attachment devices known to those skilled in the art. For purposes of this invention, the attachment device 50 is shown to be a line of adhesive extending across the width of the wrapper 36. The width of the line of adhesive 50 should be less than about 0.5 inches (about 13 mm), preferably less than about 0.25 inches (about 6.4 mm), and most preferably, less than about 0.15 inches (about 4 mm). Although the attachment device 50 is shown to be a continuous line of adhesive which extends transversely across the width of the wrapper 36, it is possible to form the line of adhesive in an intermittent fashion if desired.

Figure 4:
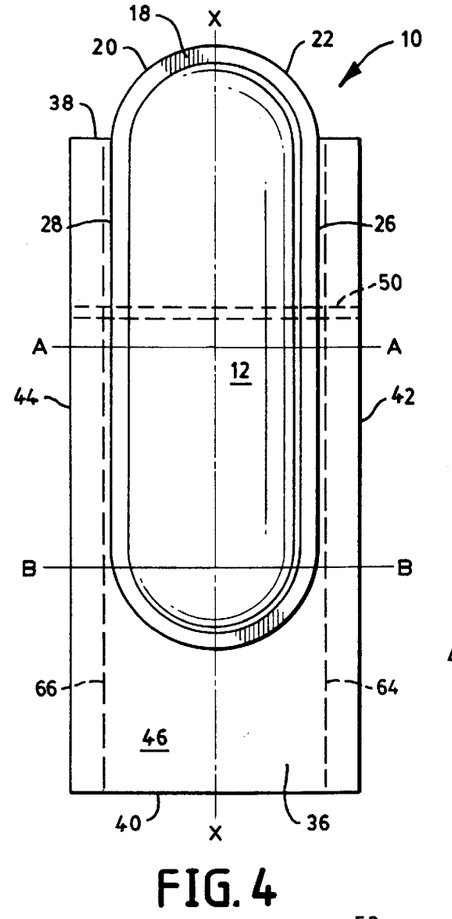
FIG. 4 is a top view of the absorbent article and wrapper showing the location of the two fold lines A—A and B—B.

Referring to FIGS. 4–7, the absorbent article 10 and the wrapper 36 are folded together as a unit about two fold axes or lines designated A—A and B—B. In FIG. 4, the absorbent article 10 is shown positioned on the wrapper 36 such that the first end 22 of the absorbent article 10 extends beyond the first end 38 of the wrapper 36 while the second end 24 of the absorbent article 10 is within the confinds of the second end 40 of the wrapper 36. This offset occurs along the longitudinal axis x—x only. The first and second longitudinal sides, 26 and 28 respectively, of the absorbent article 10 are spaced inward from the first and second longitudinal sides, 42 and 44 respectively, of the wrapper 36. Preferably, the first and second longitudinal sides, 26 and 28 respectively, of the absorbent article 10 will be spaced inward from the first and second longitudinal sides, 42 and 44 respectively, of the wrapper 36 by at least about 0.12 inches (about 3 mm). More preferably, the first and second longitudinal sides, 26 and 28 respectively, will be spaced inward from the the first and second longitudinal sides, 42 and 44 respectively, of the wrapper 36 by about 0.5 inches (about 13 mm).

Figure 5:
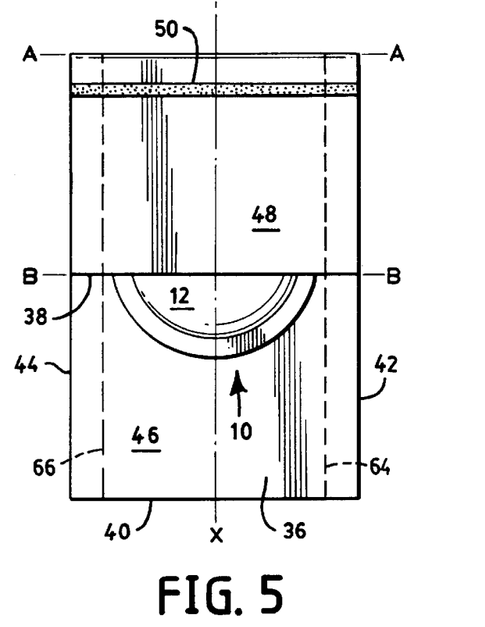
FIG. 5 is a top view of the absorbent article and wrapper having been folded along the first fold line A—A.

The absorbent article 10 and the wrapper 36 are folded along the first fold axis or line A—A to arrive at a configuration as that shown in FIG. 5. As seen in FIG. 5, the attachment device 50 is exposed so that when the remaining portion of the wrapper 36 is folded along the second fold axis or line B—B, the first major surface 46 of the wrapper 36 will come in contact with the attachment device 50 and be releasably secured thereto. The attachment device 50 is designed such that it will easily release from the first major surface 46 with a small amount of pressure.

Figure 6:
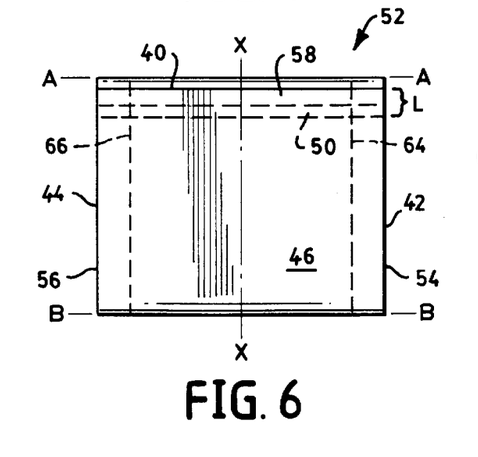
FIG. 6 is a top view of the absorbent article and wrapper having been folded a second time along the fold line B—B such that the first surface of the wrapper contacts the attachment device located on the second surface of the wrapper.

Referring to FIG. 6, the absorbent article 10 and the wrapper 36 are folded along the second fold axis or line B—B to form a package 52. The package 52 has a first side edge 54 and a second side edge 56 which are aligned parallel to one another. Preferably, the first and second side edges, 54 and 56 respectively, are aligned parallel to the first and second sides, 26 and 28 respectively, of the absorbent article 10. The package 52 will also contain a flap 58 which is formed from the wrapper 36. The flap 58 is comprised of material located between the attachment device 50 and the second end 40 of the wrapper 36. This flap 58 can vary in size but preferably has a length L which is less than about 1 inch (about 25 mm), preferably less than about 0.5 inches (about 13 mm), and more preferably, less than about 0.4 inches (about 10 mm). When the individually packaged absorbent article 10 is a sanitary napkin, the length L of the flap 58 is preferably between from about 0.3 inches to about 0.5 inches (about 7 to about 13 mm). The purpose of the flap 58 is to allow the user of the absorbent article 10 to insert one or more of her fingers or finger tips between the flap 58 and the second major surface 48 of the wrapper 36. By inserting one's fingers under the flap 58, the attachment device 50 can be easily broken. For example, the user's index finger and middle finger can be inserted beyond the attachment device 50 and the thumb can be placed on the second major surface 48 of the wrapper 50 such that by pulling outward, the package 52 can be opened.

Figure 7:
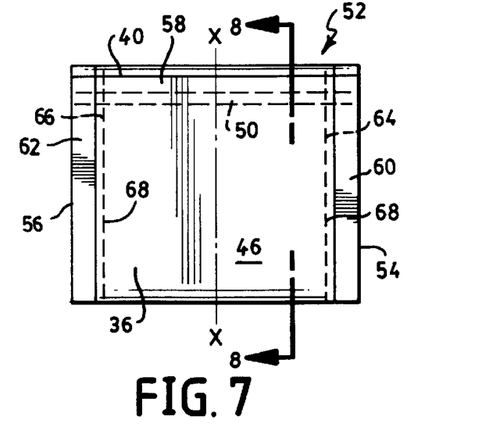
FIG. 7 is a top view of the absorbent article and wrapper folded to form a package having the side edges of the package sealed.

Referring now to FIG. 7, the package 52 is shown having a first seal 60 and a second seal 62. The two seals 60 and 62 are formed approximate or adjacent to the first and second side edges, 54 and 56 respectively. The first and second seals, 60 and 62 respectively, function to secure each of the side edges, 54 and 56 respectively, together. Each of the first and second seals, 60 and 62 respectively, can be formed by using heat, pressure, heat and pressure, an adhesive, an ultrasonic bond, or by other types of attachments known to those skilled in the art.

The first and second seals, 60 and 62 respectively, should have a width of less than about 1 inch (about 25 mm), preferably, less than about 0.5 inches (about 13 mm), and most preferably, less than about 0.25 inches (about 6.4 mm). When the absorbent article 10 is a sanitary napkin, it has been found that each of the first and second seals, 60 and 62 respectively, should have a width of from between about 1 mm to about 10 mm, and more preferably, a width of from between about 2 mm to about 7 mm.

It should be noted that the first and second seals, 60 and 62 respectively, can be made to be permanent seals. By a "permanent seal" it is meant that the material adjacent to the seal will tear, fracture, or break before the seal separates. Alternatively, the first and second seals, 60 and 62 respectively, can be frangible seals. By a "frangible seal" it is meant that the seal will separate before the material adjacent to the seal is actually torn, fractured, or separated. For purposes of this invention, it is anticipated that the first and second seals, 60 and 62 respectively, will be of the permanent type. That is, the package 52 will be opened not by breaking the first and second seals, 60 and 62 respectively, but by a different feature which will be explained shortly.

The package should also includes at least one line of perforations. The package 52, shown in FIG. 7, includes a first line of perforations 64 and a second line of perforations 66. The first and second lines of perforations, 64 and 66 respectively, are formed in the wrapper 36 adjacent to the first and second seals, 60 and 62 respectively. The first and second lines of perforations, 64 and 66 respectively, provide an easy open feature for the package 52. The first and second lines of perforations, 64 and 66 respectively, can be linear or nonlinear in configuration. When the first and second lines of perforations, 64 and 66 respectively, are linear, they can be aligned adjacent to the first and second side edges, 54 and 56 respectively, of the wrapper 36. By the phrase "adjacent to" it is meant that each of the lines of perforations 64 and 66 are spaced within about 1 inch (about 25 mm) of each of the first and second side edges, 54 and 56 respectively. Preferably, each of the lines of perforations 64 and 66 are spaced within about 0.5 inches (about 13 mm), and more preferably, within about 0.25 inches (about 6.4 mm) of each of the first and second side edges, 54 and 56 respectively. Preferably, the first and second lines of perforations, 64 and 66 respectively, are aligned approximately parallel to each of the first and second side edges, 54 and 56 respectively, of the package 52 as well as being aligned approximately parallel to the first and second sides, 26 and 28 respectively, of the absorbent article 10. When the absorbent article 10 is a sanitary napkin having an overall width of from between about 3 inches to about 4 inches (about 76 mm to about 101 mm), the wrapper 36 should have a width which is greater than that of the absorbent article 10. This will enable the first and second lines of perforations, 64 and 66 respectively, which are formed in the wrapper 36 to be spaced apart by a distance greater than the width of the absorbent article 10, for example, a distance of more than about 3 inches (about 76 mm) but less than about 5 inches (about 127 mm). Preferably, the first and second lines of perforations, 64 and 66 respectively, will be spaced apart a distance of from between about 1 inch to about 4 inches (about 25 mm to about 76 mm). For an absorbent article 10 having a width of about 4 inches (about 101 mm), the width of the wrapper 36 can be slightly larger, from about 4 inches (about 101 mm) to about 5 inches (about 127 mm).

Each of the first and second lines of perforations, 64 and 66 respectively, are made up of a plurality of slits 68 which can be arranged in a continuous, non-continuous or intermittent fashion along each of the lines of perforations, 64 and 66 respectively. Preferably, each of the first and second lines of perforations, 64 and 66 respectively, extends the entire length of the wrapper 36. However, if one wishes to limit one or both of the first and second lines of perforations, 64 and 66 respectively, such that they do not extend the entire length of the wrapper 36, this is also possible. Each of the first and second lines of perforation, 64 and 66 respectively, comprise a series of slits 68. Each slit 68 has a length of less than about 0.001 inches (about 0.02 mm), preferably, less than about 0.0005 inches (about 0.01 mm) and, more preferably, less than about 0.0001 inches (about 0.002 mm). The width of each of the slits 68 can also vary and should roughly be about ¼ of the length of the slit, more preferably, less than about ⅛ of the length of the slit. It is possible to form the slits 68 such that they extend through the entire thickness of the wrapper 36. Each of the slits 68 do not have to be of the same length and width nor be of similar configuration if one does not desire to make them so. However, for purposes of manufacturing, it is advantageous to form the slits 68 with a notched wheel or blade such that each of the slits 68 has a similar configuration and have the same dimensions.

The plurality of slits 68 which make up the first and second lines of perforations, 64 and 66 respectively, can be spaced an equal distance apart from one another, or they can be arranged such that several are spaced an equal distance apart and then an extra large land area is present before the next adjacent slit. Alternatively, the slits 68 can be equally spaced apart throughout the entire length of each line of perforations. It should be noted that for best results, the first and second lines of perforations, 64 and 66 respectively, should be identical in configuration, so that the force needed to tear or break apart the material at the first and second lines of perforations, 64 and 66 respectively, will be equal or approximately equal.

Figure 8:
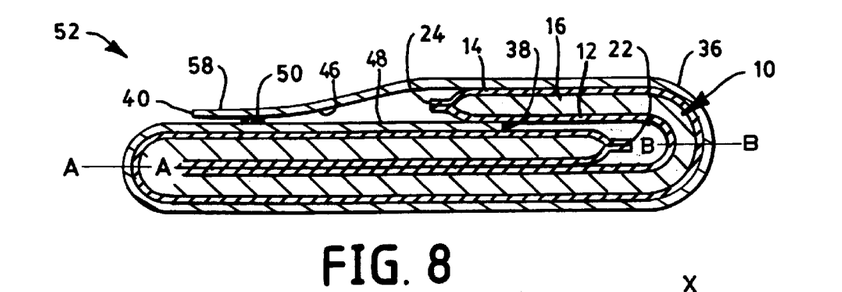
FIG. 8 is a cross-sectional view of the packaged absorbent article shown in FIG. 7 taken along line 8—8.

Referring now to FIG. 8, a cross-section of the folded absorbent article 10 and wrapper 36 are shown, clearly indicating that the attachment device 50 secures the second major surface 48 of the wrapper 36 to the first major surface 46 of the wrapper 36. The flap 58 is positioned so as to allows the user's finger(s) to be inserted thereunder and be grabbed by the thumb so as to break the attachment device 50 and provide one method of opening the package 52. In opening the package 52, the user can hold one corner of the package 52 and insert one or more of her fingers under the flap 58 with her thumb positioned against the second major surface 48 of the wrapper 36. By pulling the flap 58 outward away from the package 52, a force will be exerted on the first and second lines of perforations, 64 and 66 respectively, causing them to tear apart thereby unfolding half of the package 52. The user then grasps the first end of the package 52 and pulls upward away from the absorbent article 10. A force will be exerted in the remaining first and second lines of perforations, 64 and 66 respectively, causing them to tear apart. In so doing, one will end up with the strips 70 and 72 remaining attached to the center strip 74. The strips 70 and 72 will be equal in length to the overall length of the wrapper 36. This action will expose the absorbent article 10 which can then be attached to the inner crotch portion of an undergarment.

Figure 9:
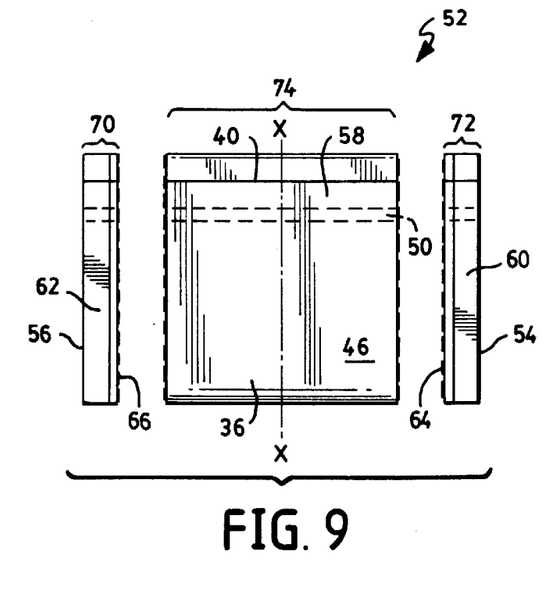
FIG. 9 is a top view of the package shown in FIG. 7 with the sealed side edges torn off of the central portion of the wrapper which surrounds the absorbent article.
Figure 10:
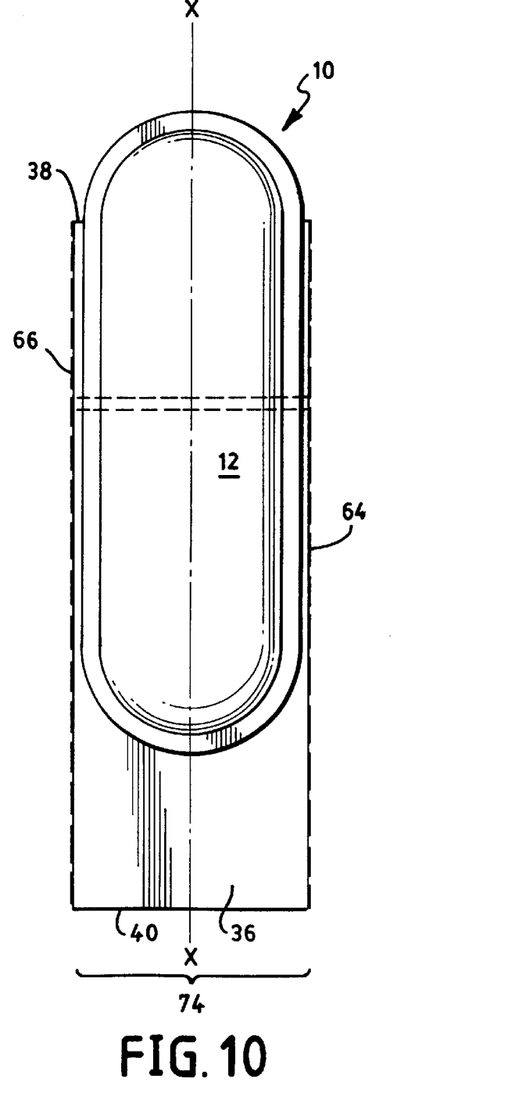
FIG. 10 is a top view of the absorbent article and wrapper after both have been unfolded from the position shown in FIG. 9.
Figure 11:
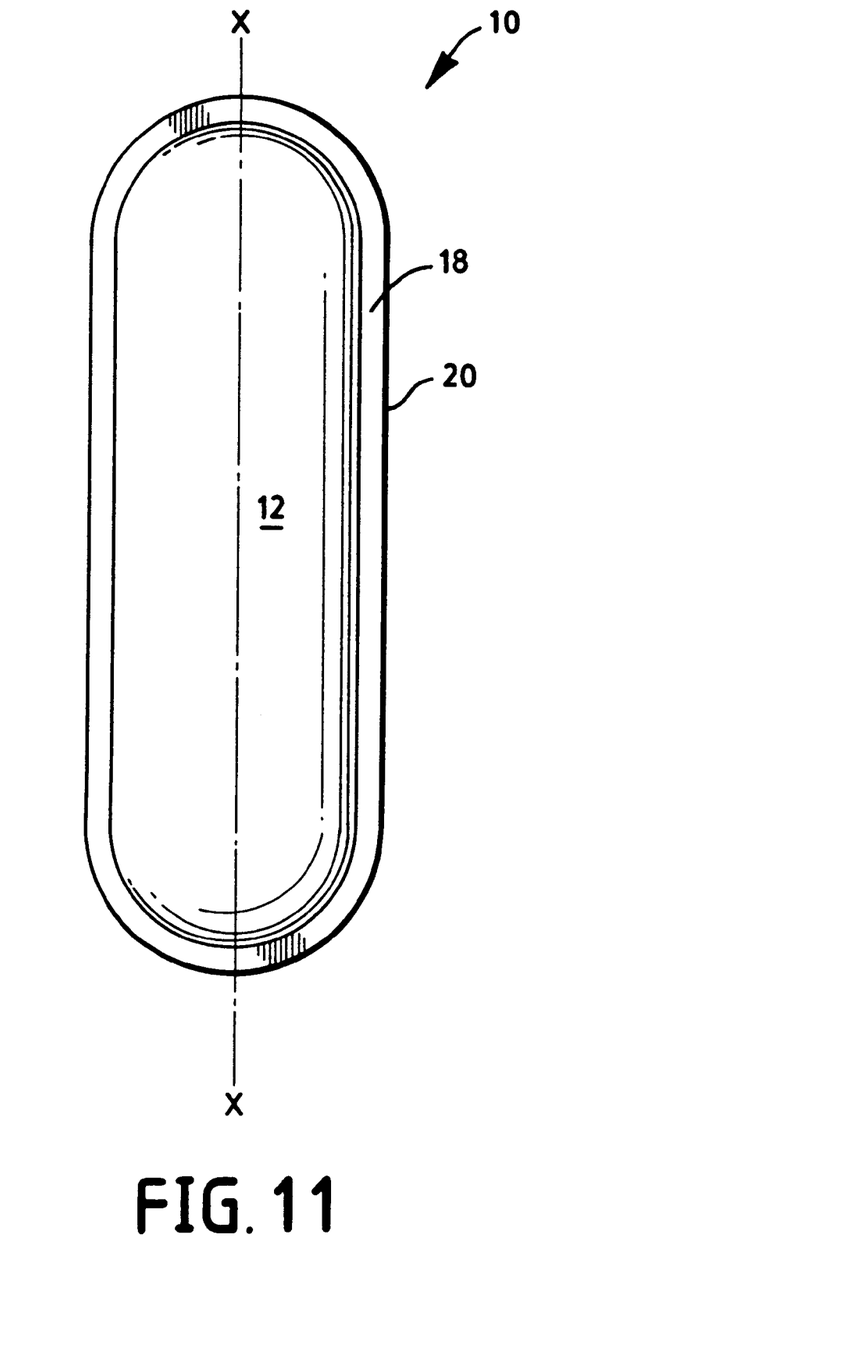
FIG. 11 is a top view of the absorbent article after it has been removed from the wrapper and is ready for use.

Referring to FIGS. 9–11, another way of opening the package 52 is depicted. This second way requires the user holds one corner of the package 52 with her left hand, between her index finger and thumb while holding the central portion of the package 52 in her right hand. By pulling outward on the material with her left hand, a strip 70 is detached from the main body of the wrapper 36. The consumer can then hold the opposite corner in her right hand while holding the central portion in her left hand and she can tear and remove a second strip 72 from the wrapper 36. This action will leave a wide central strip 74 which encloses the absorbent article 10. The width of the strips 70 and 72 can be relatively narrow, for example, they can be less than about 0.5 inches (about 13 mm), and more preferably, less than about 0.25 inches (about 6.4 mm). The user can then grasp the flap 58 between one or more fingers and her thumb, preferably between her index finger and her thumb, and pull the wrapper 36 apart such that it releases from the attachment device 50. The absorbent article 10 and the wrapper 36 can then be opened to the configuration shown in FIG. 10. The absorbent article 10 is then removed from the wrapper 36, as is shown in FIG. 11, and is ready for use. The wrapper 36 is releasably removed and separated from the garment attachment adhesive 34 because the wrapper 36 is made out of a material such as a thermoplastic film, which will not stick to the garment attachment adhesive 34. Alternatively, the wrapper 36 can be treated with a substance, such as a silicone coating, so as to facilitate the easy separation between the wrapper 36 and the garment attachment adhesive 34.

The larger central strip 74 of the wrapper 36 can be used to wrap a soiled absorbent article which the user may have removed from her undergarment prior to using the new absorbent article 10. The larger width of the central strip 74 is designed to satisfy this disposal need.

Figure 12:
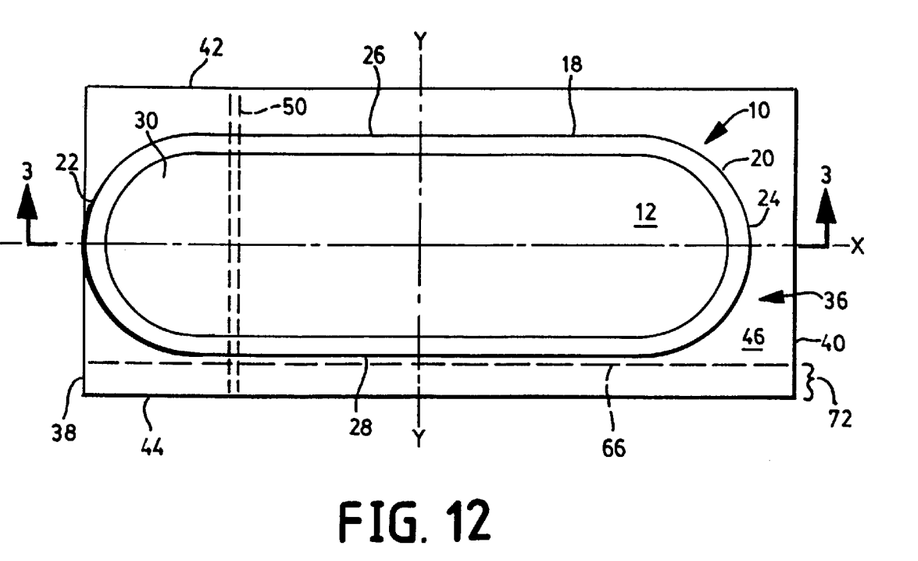
FIG. 12 is a top view of an absorbent article positioned above a rectangular shaped wrapper whereby one end of the absorbent article is flush with an end of the wrapper.

Referring now to FIG. 12, another embodiment is shown with the absorbent article 10 being positioned over the wrapper 36 such that the first end 22 of the absorbent article 10 is flush with the first end 38 of the wrapper 36. When the absorbent article 10 is arranged on the wrapper 36 in this fashion, a savings in wrapper material will occur. The amount of savings will not be as great as when the absorbent article 10 is offset beyond an end of the wrapper 36 but the savings is greater than if the absorbent article 10 was centered upon the wrapper 36.

FIG. 12 also differs from FIG. 1 in that only one line of perforations 66 is formed in the wrapper 36. The line of perforations 66 is continuous from the first end 38 to the second end 40 of the wrapper 36. When the absorbent article 10 and the wrapper 36 are folded at two fold locations as discussed previously to form a package or pouch 52, it is possible to open the package 52 by tearing along the single line of perforation 66. In so doing, the absorbent article 10 can be separated from the package 52 by simply pulling it out of the opening formed when the tear strip 72 is removed. However, for this embodiment to work, the first major surface 46 must be coated with a slippery substance, such as a silicone coating, so that the garment attachment adhesive 34 will not stick to it. The treatment or coating on the first major surface of the wrapper 46 will permit the absorbent article 10 to be easily withdrawn from the package 52. The package 52, with the opening in one side, can then be used to receive a soiled absorbent article which the consumer may have taken out of her underpants so as to discreetly dispose of the soiled absorbent article.

Figures 13, 14:
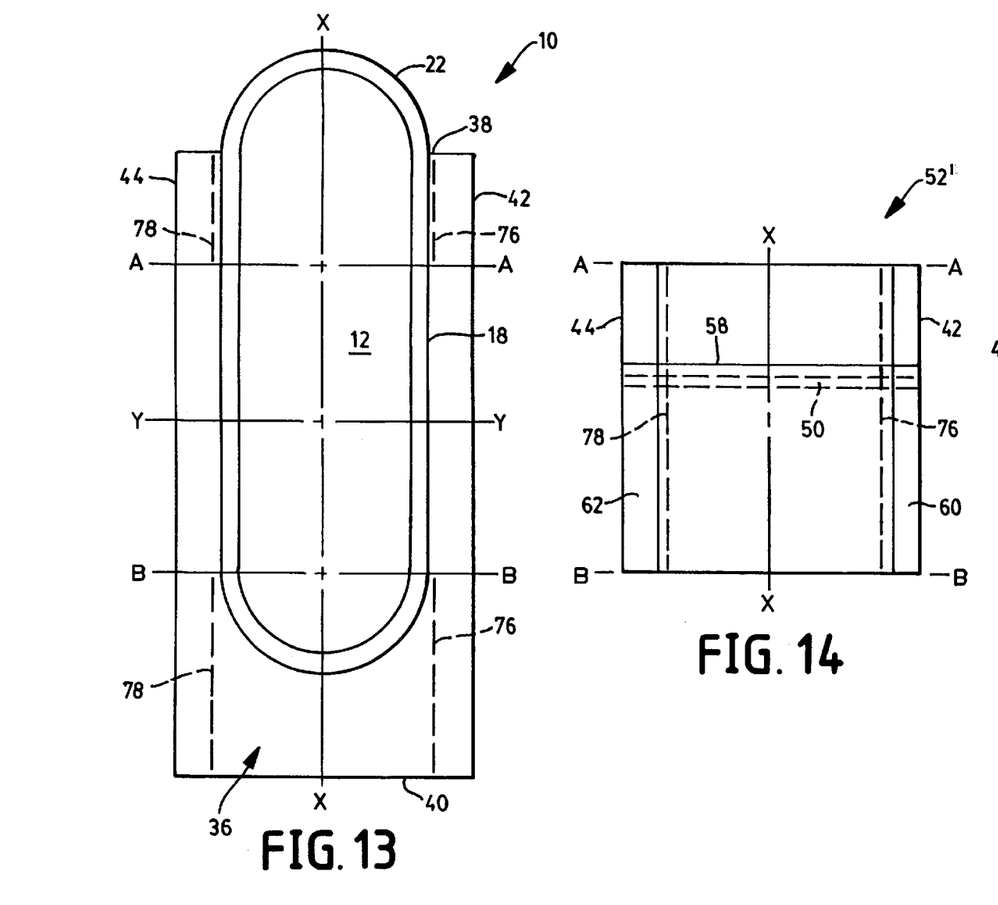
FIG. 13 is a top view of an absorbent article offset on a wrapper and the wrapper has two non-continuous lines of perforations.
FIG. 14 is a top view of the wrapper depicted in FIG. 13 after it has been folded along fold line A—A and fold line B—B showing the two lines of perforations located adjacent to the side seals.
Figure 15:
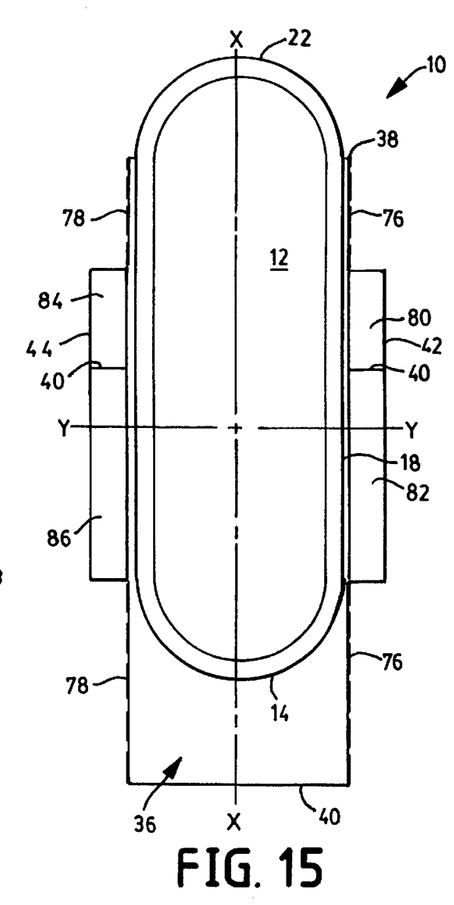
FIG. 15 is a top view of the absorbent article and wrapper after the two lines of perforations have been broken and the absorbent article and wrapper have been unfolded.
Figure 16:
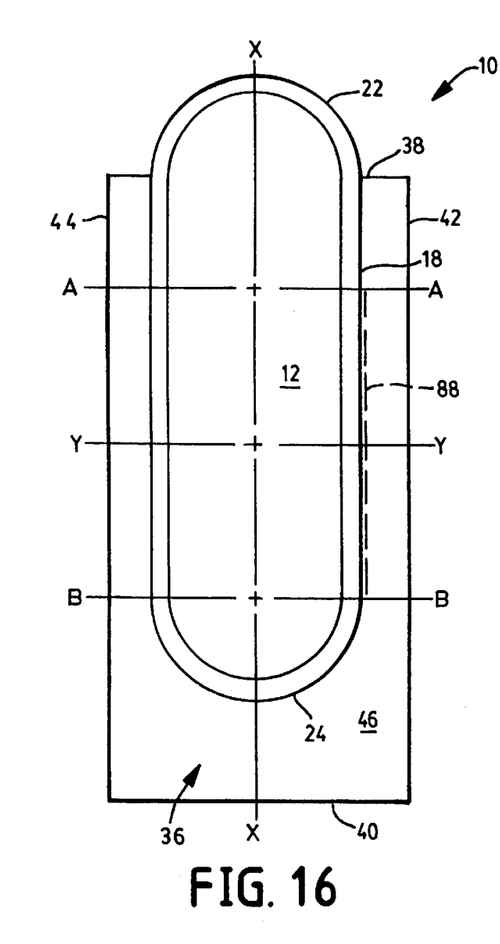
FIG. 16 is a top view of another embodiment of an absorbent article offset on a wrapper and the wrapper has a continuous line of perforations formed only in a central section thereof.

Referring to FIGS. 13–15, another alternative embodiment is shown wherein an absorbent article 10 has a first end 22 which is offset outward beyond the first end 38 of a wrapper 36. This embodiment differs from the embodiment shown in FIG. 1 in that the first and second lines of perforations, 76 and 78 respectively, are of an intermittent design. By "intermittent design" it is meant that the slits forming the first and second lines of perforations 76 and 78 are not continuous from one end of the wrapper 36 to the other end. Instead, the first and second lines of perforations, 76 and 78 respectively, are separated by a large area were no slits are present. In FIG. 13, one will notice that the first line of perforations 76 extend from the first end 38 to the fold line A—A as well as from the second end 40 to the second fold line B—B. The same is true for the second line of perforations 78 which is formed adjacent to the second side 44 of the wrapper 36. Stated another way, the first and second lines of perforations, 76 and 78 respectively, extend from the first and second ends, 38 and 40 respectively, inward toward the transverse centerline y—y but are not present between the two fold lines A—A and B—B. As mentioned earlier, the first and second lines of perforations, 76 and 78 respectively, can be aligned parallel to the first and second sides, 42 and 44 respectively, of the wrapper 36 or they can be angled relative to the first and second sides 42 and 44. When the absorbent article 10 and the wrapper 36 are folded along the fold line A—A and then along the fold line B—B, a package 52' is formed which is shown in FIG. 14.

FIG. 14 is similar to the package 52 shown in FIG. 7 except that the backside of the package 52' does not have the first and second lines of perforations, 76 and 78 respectively. The package 52' can be opened so as to produce the configuration shown in FIG. 15. As the consumer inserts her fingers under the flap 58 as pulls upward and outward, the first and second lines of perforations, 76 and 78 respectively, will break up to the first fold line A—A. The consumer will then insert her fingers under the opposite end 40 of the wrapper 36 and pull upward and outward to break the first and second lines of perforations, 76 and 78 respectively, up to the second fold line B—B. One will notice that the material located between the first and second sides, 42 and 44 respectively, and the first and second lines of perforations, 76 and 78 respectively, will form thin narrow slivers 80, 82, 84, and 86. The thin slivers 80 and 82 will remain together when the package 52' is opened as will the thin slivers 84 and 86, see FIG. 15. The central portion of the wrapper 36, which was not perforated, will retain its original width. With this embodiment, an advantage is that there are no separate pieces of material which are completely torn from the original wrapper 36, and therefore, the wrapper 36 can be disposed of as a unitary piece.

Figure 17:
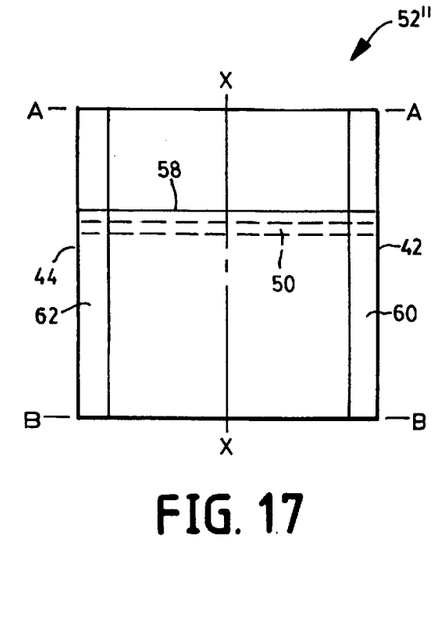
FIG. 17 is a top view of the wrapper depicted in FIG. 16 after it has been folded along fold line A—A and fold line B—B showing the absent of any lines of perforations.
Figure 18:
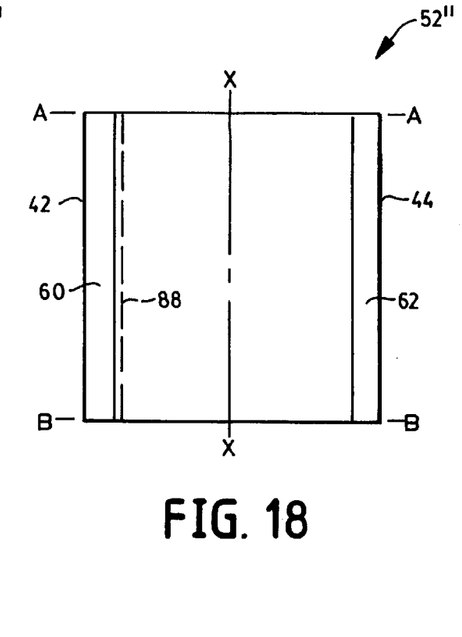
FIG. 18 is a back view of the wrapper depicted in FIG. 17 showing a single line of perforations aligned adjacent to one of the side seals.
Figure 19:
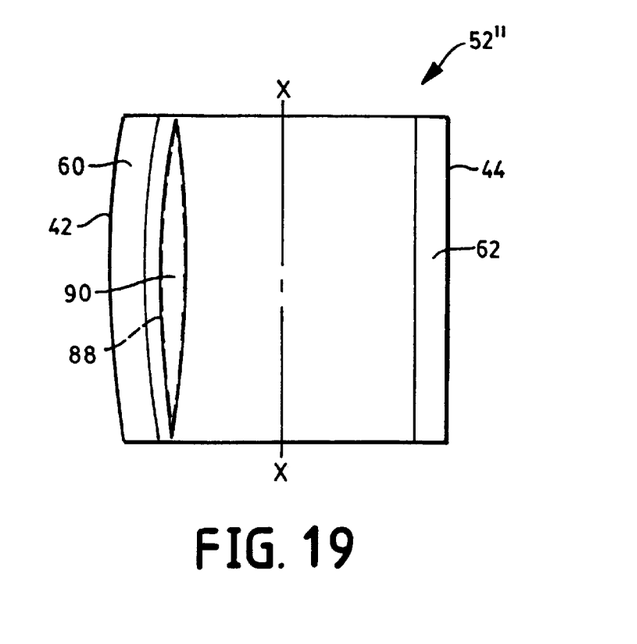
FIG. 19 is a schematic representation of the pouch shown in FIG. 18 after the line of perforations has been broken so as to form an opening through which the absorbent article can be removed.

Referring to FIGS. 16–19, still another embodiment is shown wherein an absorbent article 10 is offset on a wrapper 36. In this configuration, the first end 22 of the absorbent article 10 extends beyond the first end 38 of the wrapper 36. The difference in FIG. 16 from FIG. 1 is that only a single line of perforations 88 is formed adjacent to the first side 42 of the wrapper 36. The line of perforations 88 extends only between the fold lines A—A and B—B. The line of perforations 88 does not extend to either of the ends 38 or 40 of the wrapper 36. When the absorbent article 10 and the wrapper 36 are folded along the fold line A—A and then along the fold line B—B, a package or pouch 52" is formed. The front view of the package 52" is shown in FIG. 17 and the rear view is shown in FIG. 18. The front view of the package 52" does not exhibit any line of perforations. However, upon looking at the backside or rear view of the package 52", one will notice that the line of perforations 88 is formed and appears adjacent to the first side 42. The package 52" can have the line of perforations 88 broken, as is shown in FIG. 19, thereby creating an opening 90 through which the absorbent article 10 can be removed. It should be noted that the first major surface 46 of the wrapper 36 in FIGS. 16–19 must be treated or coated with a slippery substance, such as silicone, to facilitate removal of the absorbent article 10 from the wrapper 36. If the first major surface is not treated or coated, the garment attachment adhesive 34 may stick to the wrapper 36 and hinder removal of the absorbent article 10 from the package 52".

The package 52" can also be opened a second way by having the consumer insert her fingers under the flap 58 and use her thumb and fingers to pull upward and outward on the flap 58 so as to tear or break the first and second seal 60 and 62. This second way of opening the package 52" requires that the wrapper material be torn or fractured in order to open the package 52". Accordingly, the first method of opening the package 52" is preferred. When the package 52" is opened by breaking the line of perforations 88, the absorbent article 10 can be removed and a soiled absorbent article can be inserted through the opening 90 so as to be disposed of discreetly.

While the invention has been described in conjunction with a specific embodiment, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. An individually wrapped absorbent article comprising:
   a) an absorbent article having first and second ends, first and second sides and first and second major surfaces, said second major surface having a garment attachment adhesive secured thereto;
   b) a wrapper having first and second ends, first and second sides and first and second major surfaces, said first major surface of said wrapper being releaseably affixed to said garment attachment adhesive such that said first end of said absorbent article at a minimum is flush with said first end of said wrapper, said second end of said wrapper extends beyond said second end of said absorbent article and said first and second sides of said wrapper extend laterally outward from said first and second sides of said absorbent article, respectively;
   c) an attachment device secured to said second major surface of said wrapper approximate said first end thereof, said wrapper and said absorbent article being folded together about two fold axes such that said first major surface of said wrapper contacts said attachment device and is releaseably secured thereto to form a package, said package having first and second side edges aligned approximately parallel to said first and second sides of said absorbent article, respectively;
   d) a first seal and a second seal securing said first and second side edges together, respectively; and
   e) at least one line of perforations formed in said wrapper adjacent to one of said first and second seals, said line of perforations providing an easy open feature for said package.

2. The individually wrapped absorbent article of claim 1 wherein first and second lines of perforations are formed in said wrapper adjacent to said first and second side seals, respectively.

3. The individually wrapped absorbent article of claim 1 wherein said first end of said absorbent article extends outward beyond said first end of said wrapper.

4. The individually wrapped absorbent article of claim 1 wherein said first end of said absorbent article abuts said first end of said wrapper.

5. The individually wrapped absorbent article of claim 1 wherein said line of perforations is continuous between said first end and said second end of said wrapper.

6. The individually wrapped absorbent article of claim 1 wherein said line of perforations is intermittent between said first end and said second end of said wrapper.

7. The individually wrapped absorbent article of claim 1 wherein said line of perforations is not continuous between said first end and said second end of said wrapper.

8. An individually wrapped absorbent article comprising:
   a) an absorbent article having first and second ends, first and second sides and first and second major surfaces, said second major surface having a garment attachment adhesive secured thereto;
   b) a wrapper having first and second ends, first and second sides and first and second major surfaces, said first major surface of said wrapper being releaseably affixed to said garment attachment adhesive such that said first end of said absorbent article abuts said first end of said wrapper, said second end of said wrapper extends beyond said second end of said absorbent article and said first and second sides of said wrapper extend laterally outward from said first and second sides of said absorbent article, respectively;
   c) an attachment device secured to said second major surface of said wrapper approximate said first end thereof, said wrapper and said absorbent article being folded together about two fold axes such that said first major surface of said wrapper contacts said attachment device and is releaseably secured thereto to form a package, said package having first and second side edges aligned approximately parallel to said first and second sides of said absorbent article, respectively;
   d) a first seal and a second seal securing said first and second side edges together, respectively; and
   e) at least one line of perforations formed in said wrapper adjacent to one of said first and second seals, said line of perforations providing an easy open feature for said package.

9. The individually wrapped absorbent article of claim 8 wherein said absorbent article and said wrapper each have a length and the length of said absorbent article is equal to the length of said wrapper.

10. The individually wrapped absorbent article of claim 8 wherein said absorbent article and said wrapper each have a length and the length of said absorbent article is shorter than the length of said wrapper.

11. The individually wrapped absorbent article of claim 8 wherein said absorbent article and said wrapper each have a length and the length of said absorbent article is longer than the length of said wrapper.

12. The individually wrapped absorbent article of claim 8 wherein said first end of said absorbent article extends beyond said first end of said wrapper by at least about 0.25 inches.

13. An individually wrapped absorbent article comprising:
   a) an absorbent article having first and second ends, first and second sides and first and second major surfaces, said second major surface having a garment attachment adhesive secured thereto;
   b) a wrapper having first and second ends, first and second sides and first and second major surfaces, said first major surface of said wrapper being releaseably affixed to said garment attachment adhesive such that said first end of said absorbent article extends beyond said first end of said wrapper, said second end of said wrapper extends beyond said second end of said absorbent article and said first and second sides of said wrapper extend laterally outward from said first and second sides of said absorbent article, respectively;
   c) an attachment device secured to said second major surface of said wrapper approximate said first end thereof, said wrapper and said absorbent article being folded together about two fold axes such that said first major surface of said wrapper contacts said attachment device and is releaseably secured thereto to form a package, said package having first and second side edges aligned approximately parallel to said first and second sides of said absorbent article, respectively;

d) a first seal and a second seal securing said first and second side edges together, respectively; and e) at least one line of perforations formed in said wrapper adjacent to one of said first and second seals, said line of perforations providing an easy open feature for said package.

14. The individually wrapped absorbent article of claim 13 wherein said absorbent article and said wrapper each have a length and the length of said absorbent article is equal to the length of said wrapper.

15. The individually wrapped absorbent article of claim 13 wherein said absorbent article and said wrapper each have a length and the length of said absorbent article is shorter than the length of said wrapper.

16. The individually wrapped absorbent article of claim 13 wherein said absorbent article and said wrapper each have a length and the length of said absorbent article is longer than the length of said wrapper.

17. An individually wrapped absorbent article comprising:

a) an absorbent article having first and second ends, first and second longitudinal sides and first and second major surfaces, said second major surface having a garment attachment adhesive secured thereto;

b) a wrapper having first and second ends, first and second longitudinal sides and first and second major surfaces, said first major surface of said wrapper being releaseably affixed to said garment attachment adhesive such that said first end of said absorbent article extends beyond said first end of said wrapper by at least about 0.25 inches, said second end of said wrapper extends beyond said second end of said absorbent article and said first and second longitudinal sides of said wrapper extend laterally outward from said first and second longitudinal sides of said absorbent article, respectively;

c) an attachment device secured to said second major surface of said wrapper approximate said first end thereof, said wrapper and said absorbent article being folded together about two fold axes such that said first major surface of said wrapper contacts said attachment device and is releaseably secured thereto to form a package, said package having first and second side edges aligned approximately parallel to said first and second longitudinal sides of said absorbent article, respectively;

d) a first seal and a second seal securing said first and second side edges together, respectively; and e) first and second lines of perforations formed in said wrapper adjacent to and inward of said first and second seals, respectively, said lines of perforations providing an easy open feature for said package.

18. The individually wrapped absorbent article of claim 17 wherein said first end of said absorbent article extends beyond said first end of said wrapper by at least about 0.5 inches.

19. The individually wrapped absorbent article of claim 17 wherein said second end of said wrapper extends beyond said second end of said absorbent article by at least about 0.25 inches.

20. The individually wrapped absorbent article of claim 17 wherein said first end of said absorbent article extends beyond said first end of said wrapper by an amount from between about 0.25 inches to about 2 inches.

21. The individually wrapped absorbent article of claim 17 wherein said first end of said absorbent article extends beyond said first end of said wrapper by an amount from between about 0.25 inches to about 1 inch.

22. An individually wrapped absorbent article comprising:

a) an absorbent article having first and second ends, first and second longitudinal sides and first and second major surfaces, said second major surface having a garment attachment adhesive secured thereto;

b) a wrapper having first and second ends, first and second longitudinal sides and first and second major surfaces, said first major surface of said wrapper being releaseably affixed to said garment attachment adhesive such that said first end of said absorbent article extends beyond said first end of said wrapper by at least about 0.25 inches, said second end of said wrapper extends beyond said second end of said absorbent article and said first and second longitudinal sides of said wrapper extend laterally outward from said first and second longitudinal sides of said absorbent article, respectively;

c) a line of adhesive secured to said second major surface of said wrapper approximate said first end thereof, said wrapper and said absorbent article being folded together about two fold axes such that said first major surface of said wrapper contacts said attachment device and is releaseably secured thereto to form a package, said package having first and second side edges aligned approximately parallel to said first and second longitudinal sides of said absorbent article, respectively;

d) a first seal and a second seal securing said first and second side edges together, respectively; and e) first and second lines of perforations formed in said wrapper adjacent to and inward of said first and second seals, respectively, said lines of perforations providing an easy open feature for said package.

23. The individually wrapped absorbent article of claim 22 wherein said line of adhesive extends transversely across said second major surface of said wrapper from said first side to said second side.

24. The individually wrapped absorbent article of claim 22 wherein said line of adhesive is continuous.

25. The individually wrapped absorbent article of claim 22 wherein said line of adhesive is intermittent.

26. The individually wrapped absorbent article of claim 22 wherein said second end of said wrapper extends beyond said second end of said absorbent article by at least about 0.25 inches.

27. The individually wrapped absorbent article of claim 22 wherein said first end of said absorbent article extends beyond said first end of said wrapper by an amount from between about 0.25 inches to about 1 inch.

28. An individually wrapped absorbent article comprising:

a) an absorbent article having first and second ends, first and second sides and first and second major surfaces, said second major surface having a garment attachment adhesive secured thereto;

b) a wrapper having first and second ends, first and second sides and first and second major surfaces, said first major surface of said wrapper being releaseably affixed to said garment attachment adhesive such that said first end of said absorbent article at a minimum is flush with said first end of said wrapper, said second end of said wrapper extends beyond said second end of said absorbent article and said first and second sides of said wrapper extend laterally outward from said first and second sides of said absorbent article, respectively;

c) an attachment device secured to said second major surface of said wrapper approximate said first end thereof, said wrapper and said absorbent article being folded together about two fold axes such that said first major surface of said wrapper contacts said attachment device and is releaseably secured thereto to form a package, said package having first and second side edges aligned approximately parallel to said first and second sides of said absorbent article, respectively;

d) a first seal and a second seal securing said first and second side edges together, respectively; and e) at least one line of perforations formed in said wrapper adjacent to one of said first and second seals, said line of perforations extending over a portion of the length of said wrapper to provide an easy open feature for said package.

29. The individually wrapped absorbent article of claim 28 wherein a first line of perforations is formed in said wrapper adjacent to one of said first and second sides and extends along a portion of the length of said wrapper.

30. The individually wrapped absorbent article of claim 28 wherein first and second lines of perforations are formed in said wrapper and each of said lines of perforations extend along a portion of the length of said wrapper.

31. The individually wrapped absorbent article of claim 30 wherein said wrapper has a transverse centerline and both of said first and second lines of perforations extend inward from said first and second ends of said wrapper toward said transverse centerline.

* * * * *